United States Patent [19]

Giraud

[11] Patent Number: 4,789,686

[45] Date of Patent: Dec. 6, 1988

[54] PROCESS FOR THE PREPARATION OF AN AQUEOUS SOLUTION OF THE SODIUM SALT OF METHIONINE

[75] Inventor: Jean Giraud, Neris-les-Bains, France

[73] Assignee: AEC-Sociate de Chimie Organique et Biologique, Commentry, France

[21] Appl. No.: 73,159

[22] Filed: Jul. 14, 1987

[30] Foreign Application Priority Data

Jul. 17, 1986 [FR] France ................................ 86 10399

[51] Int. Cl.⁴ ............................................. A01K 13/00
[52] U.S. Cl. .................................... 514/562; 514/183; 514/359; 514/389; 514/390; 514/476; 514/553; 514/554; 514/579; 514/584; 514/706; 562/554; 562/559; 562/575
[58] Field of Search ............... 514/183, 359, 389, 390, 514/476, 579, 584, 706, 562, 553, 554; 562/559, 554, 575

[56] References Cited

U.S. PATENT DOCUMENTS

| | | | |
|---|---|---|---|
| 2,642,459 | 6/1953 | White | 562/575 |
| 3,920,737 | 11/1975 | Horisawa et al. | 562/559 |
| 4,233,461 | 11/1980 | Kawabata et al. | 562/554 |
| 4,272,631 | 6/1981 | Schaaf et al. | 562/575 |

FOREIGN PATENT DOCUMENTS

| | | |
|---|---|---|
| 934407 | 1/1972 | France . |
| 1532723 | 7/1981 | France . |
| 1199614 | 5/1980 | United Kingdom . |

*Primary Examiner*—Morton Foelak
*Assistant Examiner*—S. A. Acquah
*Attorney, Agent, or Firm*—Stevens, Davis, Miller & Mosher

[57] ABSTRACT

A concentrated aqueous solution of the sodium salt of methionine, which is practically free from inorganic salts, is produced from the medium resulting from the hydrolysis of 5-($\beta$-mercaptoethyl)hydantoin.

3 Claims, No Drawings

PROCESS FOR THE PREPARATION OF AN AQUEOUS SOLUTION OF THE SODIUM SALT OF METHIONINE

The present invention relates to the preparation of an aqueous solution of the sodium salt of methionine, which can be used as an additive in feeding-stuffs for livestock.

Methionine, which is an essential amino acid, is used in small doses, generally less than 1%, as an additive in animal feeding stuffs. It is particularly important to be able to disperse methionine homogeneously in the feed and to be able to determine the methionine content accurately.

The use of methionine in the liquid form has advantages compared with its use in the crystalline form as the handling and the determination thereof are made easier. The use of a liquid product enables a homogeneous dispersion to be achieved at concentrations which can easily be controlled.

Because methionine is sparingly soluble in water, it cannot be used as such in aqueous solution because of the large volumes which would need to be handled. However, alkali metal salts of methionine, and in particular the sodium salt, have greater water-solubility and can be obtained in sufficiently concentrated solutions which are particularly well suited for this purpose.

Solutions of the sodium salt of methionine (sodium methioninate) may be prepared by dissolving methionine in aqueous sodium hydroxide solution. However, this method of preparation is not economically advantageous because of the need for prior isolation of methionine before it is dissolved in a suitable medium.

The preparation of aqueous solutions of sodium methioninate by the hydrolysis of 5-($\beta$-methylmercaptoethyl)hydantoin using an excess of sodium hydroxide and/or sodium carbonate and/or lime is known from French Patent Applications FR-2,499,560, FR-2,499,563, FR-2,499,564, FR-2,499,565 and FR-2,499,566. However, during the hydrolysis, large quantities of sodium and/or calcium carbonate are formed and they must be removed by suitable treatments (concentration, precipitation, filtration and the like). Additionally, these methods lead to the production of a carbonate which cannot be put into use directly and which requires an additional treatment for the recovery of the carbon dioxide required in the synthesis of 5-($\beta$-mercaptoethyl)hydantoin.

It has now been found, and this forms the subject of the present invention, that a concentrated aqueous solution of sodium methioninate which is practically free from inorganic salts may be obtained from an aqueous solution containing the sodium salt of methionine and a substantially equivalent quantity of sodium carbonate obtained by hydrolysis of 5-($\beta$-methylmercaptoethyl)-hydantoin by adding to the said solution a quantity of sulphuric acid sufficient to neutralize all the sodium carbonate and, optionally, the sodium methioninate, recovering the carbon dioxide formed, concentrating the reaction medium after adding, if required, a quantity of sodium hydroxide sufficient to salify the methionine, so as to provide a sufficient concentration of the sodium salt of methionine, separating the sodium sulphate precipitated by filtration, and isolating a filtrate containing the sodium salt of methionine practically free from inorganic salts which can be used directly in animal feeding-stuffs.

The hydrolysis of 5-($\beta$-methylmercaptoethyl)hydantoin with sodium hydroxide gives a solution containing methionine, e.g. in a concentration of 10 to 20% by weight, essentially in the form of sodium methioninate, and sodium carbonate in a practically equivalent quantity. When sodium carbonate solution is treated with sulphuric acid at a high temperature, for example in the region of 100° C., neutralization of sodium carbonate and sodium bicarbonate, heat decomposition of sodium bicarbonate into sodium carbonate and carbon dioxide, and sodium sulphate formation occur simultaneously.

Moreover, it is known that the solubility of sodium sulphate is a concentrated solution of sodium methioninate does not vary greatly with temperature.

The process of the present invention may be operated by adding slowly, at a temperature in the region of 100° C., to the medium resulting from the hydrolysis of 5-($\beta$-mercaptoethyl)hydantoin, the quantity of sulphuric acid required for the complete neutralization of the sodium carbonate and then in concentrating the medium so as to have a sufficient sodium methioninate concentration, while recovering the carbon dioxide, and separating the sodium sulphate which precipitates from the sodium methioninate solution by filtration.

The process of the present invention may also be operated by neutralizing all the sodium present in the medium resulting from the hydrolysis of 5-($\beta$-methylmercaptoethyl)hydantoin (sodium methioninate and sodium carbonate) with sulphuric acid, salifying the methionine with a sufficient quantity of sodium hydroxide and, after concentrating the solution and recovering the carbon dioxide, separating the sodium sulphate precipitated from the sodium methioninate solution.

As the solubility of sodium sulphate in a concentrated sodium methioninate solution does not vary greatly with temperature, the separation of sodium sulphate by filtration may advantageously be carried out at a high temperature (in the region of 100° C). As a result, the filtration is made easier, given that the viscosity of the medium is lower than at a lower temperature.

The sodium methioninate solution obtained by the process of the present invention, which may contain, for example, 46 to 55% of sodium methioninate, contains a low proportion of sodium sulphate, generally less than 1% (w/v). Moreover, practically pure sodium sulphate is obtained as a by-product which can be used directly without further purification.

The following Examples illustrate the invention.

EXAMPLE 1

A quantity of sulphuric acid, sufficient to neutralize the sodium carbonate so that the pH of the medium (determined at a temperature of about 20° C.) is not below 10, is added to a 5-($\beta$-methylmercaptoethyl)-handantoin saponification medium (1,000 g) containing methionine (164.6 g, or 1.105 mol) in the form of the sodium salt and sodium carbonate (98.32 g), at a temperature in the region of 100° C. The carbon dioxide evolved is recovered. The solution obtained is concentrated so that the sodium methioninate concentration is between 46 and 55%. The sulphate which precipitates is separated by filtration at 100° C. A filtrate (325 g) with the following composition is thereby obtained:

sodium methioninate: 52% (w/v)
sodium sulphate: 0.52% (w/v)

The rate of recovery of carbon dioxide is 96%.

EXAMPLE 2

A quantity of sulphuric acid sufficient to neutralize the entire sodium content is slowly added to a 5-(β-methylmercaptoethyl) hydantoin saponification medium (1,000 g) containing methionine (164.3 g, or 1.103 mol) in the form of the sodium salt and a total of 2.84 gramatom of sodium, at a temperature in the region of 100° C. The carbon dioxide is recovered. The mixture is heated for a further period of 1 hour at 100° C. to remove the residual carbon dioxide. 50% (w/v) sodium hydroxide (62.5 cc), i.e. the quantity sufficient to neutralize the methionine, is then added. The solution is concentrated so that the sodium methioninate concentration is between 46 and 52%. The sodium sulphate which precipitates is separated by filtration at elevated temperature. A filtrate (342 g) with the following composition is thereby obtained:

sodium methioninate: 51.2% (w/v)
sodium sulphate: (0.61% (w/v)

The rate of recovery of carbon dioxide is 99%.

I claim:

1. A process for the preparation of a concentrated aqueous solution of the sodium salt of methionine, practically free from inorganic salts, from an aqueous solution containing the sodium salt of methionine and a substantially equivalent quantity of sodium carbonate obtained by hydrolysis of 5-(β-methylmercaptoethyl)-hydantoin with sodium hydroxide, which comprises adding to the said solution a quantity of sulphuric acid sufficient to neutralize all the sodium carbonate and, optionally, the sodium methioninate, recovering the carbon dioxide formed, concentrating the reaction medium after adding, if required, a quantity of sodium hydroxide to salify the methionine 46 to 52%, so as to provide a sufficient concentration of the sodium salt of methionine, separating the sodium sulphate precipitated by filtration, and isolating a filtrate containing the sodium salt of methionine practically free from inorganic salts which can be used directly in animal feeding-stuffs.

2. Process according to claim 1 in which the sodium sulphate is removed by filtration at about 100° C.

3. Process according to claim 1 in which the aqueous solution starting material contains up to 20% of methionine as the sodium salt.

* * * * *